(12) United States Patent
Kakuda et al.

(10) Patent No.: US 6,187,967 B1
(45) Date of Patent: Feb. 13, 2001

(54) PROCESS OF PRODUCING ADAMANTANOLS

(75) Inventors: Minoru Kakuda, Chiba-ken; Takanobu Okamoto, Ibaraki-ken; Takashi Onozawa, Ibaraki-ken; Hiroshi Kurata, Ibaraki-ken, all of (JP)

(73) Assignee: Mitsubishi Gas Chemical Company, Inc., Tokyo (JP)

( * ) Notice: Under 35 U.S.C. 154(b), the term of this patent shall be extended for 0 days.

(21) Appl. No.: 09/493,207

(22) Filed: Jan. 28, 2000

(30) Foreign Application Priority Data

Jan. 29, 1999 (JP) .................................................. 11-022198
Jun. 1, 1999 (JP) .................................................. 11-153456

(51) Int. Cl.⁷ .................................................. C07C 35/22
(52) U.S. Cl. .............................................................. 568/818
(58) Field of Search .............................................. 568/818

(56) References Cited

FOREIGN PATENT DOCUMENTS

| | | |
|---|---|---|
| 0844228 | 5/1998 | (EP) . |
| 2-104553 | 4/1990 | (JP) . |
| 2-196744 | 8/1990 | (JP) . |
| 3-118342 | 5/1991 | (JP) . |
| 5-51334 | 3/1993 | (JP) . |
| 8-38909 | 2/1996 | (JP) . |
| 9-87216 | 3/1997 | (JP) . |
| 9-327626 | 12/1997 | (JP) . |
| 10-204014 | 8/1998 | (JP) . |
| 10-286467 | 10/1998 | (JP) . |

OTHER PUBLICATIONS

Bressan, J. Mol. Catal., vol. 71(2), pp. 149–152, 1992.*
Bressan, J. Mol. Catal. vol. 77(3), pp. 283–288, 1992.*
Goldstein, J. Chem. Soc., Chem. Commun., pp. 21–22, 1991.*
Bressan, J. Chem. Soc., Chem. Commun., pp. 421–423, 1989.*
Mello, et al., "Oxidations by Methyl(trifluoromethyl)dioxirane. Oxyfunctionalization of Saturated Hydrocarbons", J. Am. Chem. Soc. 1989, pp. 6749–6757.
M. Bressan et al., "Selective Oxidation of Alkanes and Ethers Mediated by Ruthenium (II) Complexes", J. Chem. Soc., 1989, pp. 421–423.
Database WPI, Derwent Publications, XP–002137292(1st page of Abstract of JP5051334), Mar. 2, 1993 and full abstract of JP5051334(19930302).

* cited by examiner

*Primary Examiner*—Michael L. Shippen
(74) *Attorney, Agent, or Firm*—Antonelli, Terry, Stout & Kraus, LLP

(57) ABSTRACT

Adamantanols are produced in high selectivity and high yields by hydroxylation of adamantane compounds in a specific two-phase solvent system of water and an organic solvent in the presence of a ruthenium compound and hypochlorous acid or its salt. Adamantanediols transfer into the organic phase by adding a specific alcohol to a reaction liquid containing the adamantanols, thereby facilitating extraction of the adamantanediols. The ruthenium compound transfers into the water phase by treating the reaction liquid with alkali prior to the addition of the alcohol and precipitates therein, thereby facilitating the recovery of the ruthenium compound.

14 Claims, No Drawings

PROCESS OF PRODUCING ADAMANTANOLS

FIELD OF THE INVENTION

The present invention relates to a process of producing adamantanols useful as raw materials for high performance polymers, synthetic lubricants and plasticizers, and as intermediates for preparing organic chemicals such as pharmaceutical compounds and agricultural compounds.

BACKGROUND OF THE INVENTION

As the method of producing adamantanepolyols, Japanese Patent Application Laid-Open No. 2-104553 discloses a method using chromic acid. Japanese Patent Application Laid-Open No. 3-118342 and Japanese Patent No. 2678784 teach methods of hydrolyzing a brominated adamantane. Japanese Patent Application Laid-Open Nos. 8-38909, 9-327626 and 10-286467 disclose oxidization of adamantane compounds by oxygen in the presence of imide compound catalyst. Japanese Patent Application Laid-Open No.9-87216 discloses a metalloporphyrin-catalyzed oxidization of adamantane compounds by air. Japanese Patent Application Laid-Open No. 5-51334 uses ruthenium catalysts and peroxy acids. J. Am. Chem. Soc., 111, 6749 (1989) discloses a method of using dioxirane derivatives. However, the major problems of the proposed methods are in the complicated reaction systems and low yields.

An object of the present invention is to provide a method of selectively producing adamantanols from adamantane compounds in high yields.

Another object of the present invention is to provide a method of selectively producing adamantanols from adamantane compounds in high yields, where the extraction of adamantanediols is easy.

Still another object of the present invention is to provide a method of selectively producing adamantanols from adamantane compounds in high yields, where ruthenium compound is efficiently recovered.

SUMMARY OF THE INVENTION

As a result of extensive studies on the above problems in the known methods, the inventors have found that adamantanols are obtained with high selectivity and in high yields by hydroxylation of adamantane compounds catalyzed by a ruthenium compound in a specific two-phase solvent system of water and an organic solvent.

The inventors have further found that the adamantanediols transfers into an organic phase to make the extraction operation easy by adding a specific alcohol to a reaction liquid after the hydroxylation of the adamantane compounds. In addition, it has been found that the ruthenium compound catalyst is easily recovered from the reaction liquid by treating the reaction liquid with alkali prior to the addition of the alcohol. The present invention has been accomplished based on these findings.

Thus, in a first aspect of the present invention, there is provided a process of producing adamantanols comprising a step of hydroxylating an adamantane compound in the presence of a ruthenium compound and hypochlorous acid or its salt.

In a second aspect of the present invention, there is provided a process of producing adamantanols in which the hydroxylation is carried out in two-phase solvent system of water and an organic solvent.

In a third aspect of the present invention, there is provided a process of producing adamantanediols comprising a step of hydroxylating an adamantane compound in a two-phase solvent system of water and an organic solvent in the presence of a ruthenium compound and hypochlorous acid or its salt to obtain a reaction liquid; and a step of adding an alcohol having 4 to 8 carbon atoms to the reaction liquid, thereby transferring adamantanediols into the organic phase.

DETAILED DESCRIPTION OF THE INVENTION

Adamantane compounds used in the present invention as the starting materials are represented by the following formula:

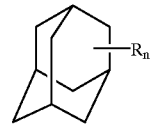

wherein Rn is independently alkyl group, aryl group, cycloalkyl group, alkoxyl group, aryloxy group, acyloxy group or halogen atom, and suffix "n" is an integer from 0 to 14, with the proviso that at least two bridge-head carbons are not substituted by $R_n$.

In the above formula, the alkyl group may be $C_1$–$C_{10}$ alkyl such as methyl, ethyl, propyl, butyl and hexyl, preferably $C_1$–$C_6$ alkyl and more preferably $C_1$–$C_4$ alkyl. The aryl group may be phenyl and naphthyl, and the cycloalkyl may be cyclohexyl or cyclooctyl. The alkoxyl group may be $C_1$–$C_{10}$ alkoxyl such as methoxyl, ethoxyl, propoxyl, butoxyl and hexyloxy. The aryloxy group may be phenoxyl. The acyloxy group may be $C_2$–$C_6$ acyloxy such as acetyloxy, propionyloxy and butyryloxy. The halogen atom may be chlorine, bromine and iodine.

The adamantanols referred to in the present invention may include adamantanemonol, adamantanediol, adamantanetriol and adamantanetetraol, and more specifically, 1-adamantanol, 1,3-adamantanediol, 1,2-adamantanediol, 1,4-adamantanediol, etc. The adamantanols may have substituent $R_n$ mentioned above.

In the present invention, the adamantane compounds are hydroxylated by a ruthenium compound of high oxidation state of VI to VIII which is generated by the reaction of a ruthenium compound and hypochlorous acid or its salt. The ruthenium compound usable in the present invention may include metallic ruthenium, ruthenium dioxide(IV), ruthenium tetraoxide(VIII), ruthenium(III) hydroxide, ruthenium (III) chloride, ruthenium(III) bromide, ruthenium(III) iodide, ruthenium(IV) sulfate, and hydrates thereof. The ruthenium compound may be used alone or in combination of two or more. The ruthenium compound is used in an amount of 0.001 to 2 mol, preferably 0.01 to 2 mol, more preferably 0.01 to 0.4 mol, and particularly preferably 0.05 to 0.4 mol per one mol of the adamantane compound. An amount less than the above range decreases the reaction rate, and an amount more than the above range results in the use of a large amount of expensive ruthenium compound, each being undesirable for industrial process.

The salt of hypochlorous acid may include sodium salt and potassium salt, and sodium hypochlorite is preferably used in view of easy availability and low cost. Hypochlorous acid and its salt are usually used in the form of aqueous solution having a concentration regulated within a range of 0.01 to 4.7 mmol/g, preferably 0.07 to 2 mmol/g. Commercially available is 12% by weight (1.6 mmol/g) aqueous solution of sodium hypochlorite. The concentration of aqueous solution of hypochlorous acid or its salt largely affects the selectivity of the adamantanediols. When the concentration is lower than the above range, the extraction efficiency of the adamantanediols is poor due to a large amount of water phase. When higher than the above range, the increase in the concentration of the adamantanediols in the organic phase accelerates side reactions to reduce the yield. If appropriate, in place of hypochlorous acid or its salt, peracetic acid, periodic acid, bromic acid and salts thereof may be used.

Hypochlorous acid or its salt is used in an amount of 0.5 to 4 mol, preferably 1 to 3 mol per one mol of the adamantane compound. When the addition amount is larger than the above range, the selectivity from the adamantane compounds to the adamantanols is extremely low, and the reaction is inefficient due to a large amount of the adamantane compounds remaining unreacted when smaller than the above range. Hypochlorous acid or its salt may be added intermittently or continuously.

The organic solvent usable in the present invention may be selected from solvents which are less compatible with water, capable of well dissolving the ruthenium compound with high oxidation state and inert to the reaction of the present invention. If highly compatible with water, the recovery of the solvent becomes costly, and the reaction hardly proceeds if the organic solvent is poor in dissolving the ruthenium compound with high oxidation state. Examples of the organic solvent are alkyl halides such as dichloromethane, 1,2-dichloroethane, chloroform, carbon tetrachloride, 1,1,2-trichloroethane, 1,4-dichlorobutane, and 1,6-dichlorohexane; esters such as methyl acetate, ethyl acetate such as isopropyl acetate; aryl halides such as hexachlorobenzene and 1,1,1-trifluorotoluene; and hydrocarbons such as hexane, heptane and octane. Of the above organic solvents, 1,2-dichloroethane and ethyl acetate are preferable. The above organic solvent may be used alone or in combination of two or more. The amount of the solvent to be used is 0.1 to 20 parts by weight, preferably 1 to 10 parts by weight per one part by weight of the starting adamantane compound. When the amount is less than the above range, the reaction rate is extremely low because a major part of the adamantane compound is not dissolved in the organic phase. An amount exceeding the above range deteriorates the reaction efficiency. The weight ratio of water and organic solvent in two-phase solvent system is preferably 1:2 to 1:20.

The reaction apparatus should have a pH controller to control the addition of an aqueous solution of hypochlorous acid or its salt. If an aqueous solution of hypochlorous acid or its salt is added at a constant rate without controlling the addition, side reactions frequently occur in later stage of the reaction due to increased concentration of hypochlorous acid or its salt in the water phase, this resulting in decrease of adamantanediols.

The optimum reaction pH depends on reaction conditions such as the kind of ruthenium compound and the molar ratio of the adamantane compound to the ruthenium compound. For example, the optimum reaction pH is around 3 when 15 g of ruthenium chloride(III) is used to 100 g of an adamantane compound, and around 7 when 5 g or ruthenium chloride(III) is used to 100 g of an adamantane compound. When the reaction pH is higher than the optimum pH in respective reaction conditions, the yield of adamantanediols decreases due to side reactions, while the reaction rate is low when the reaction pH is lower than the optimum pH because the formation of the ruthenium compound with high oxidation state is difficult due to lack of hypochlorous acid or its salt being added. The optimum pH range is 0.1 to 11 when the catalyst is used in the amount range mentioned above.

The reaction temperature is 10 to 100° C., preferably 40 to 70° C. A reaction temperature lower than the above range extremely lowers the reaction rate. When the reaction temperature is higher than the above range, the selectivity is decreased due to decomposition of hypochlorous acid or its salt and increased side reactions. Since the reaction is exothermic, the reaction apparatus is preferred to have a cooling device to maintain the reaction The reaction time is 200 to 500 minutes. The reaction may be carried out in any of known reaction apparatus equipped with a stirring device in either batch-wise or continuous manner.

The organic solvent containing a large amount of the catalyst may be used, without separating the catalyst, in the next run of the reaction by allowing hypochlorous acid or its salt to remain in separating the water phase and the organic phase after the reaction. Alternatively, the catalyst may be reused after recovering from the organic solvent. A slight amount of the catalyst in the water phase may be recovered by extracting the water phase with an organic solvent usable as the reaction solvent. By the extraction, adamantanemonol in the water phase is also extracted. Then, crude adamantanediols are obtained by concentrating the resultant water phase.

Of the adamantanols produced in the present invention, adamantanemonol is more soluble in the organic solvent than in water, whereas polyols such as adamantanediol, etc. is more soluble in water than in the organic solvent. By utilizing this solubility difference, the adamantanemonol and the polyols are separated in the reaction system. Namely, a substantial part of the adamantanemonol formed by the hydroxylation of the adamantane compound is dissolved in the organic phase. The adamantanemonol is further hydroxylated to form the adamantanediol to transfer into the water phase. The ruthenium in high oxidation state serving as the catalyst is highly compatible with the organic solvent and a major part thereof is dissolved in the organic phase. Therefore, the adamantanediol transferred into the water phase is less subjected to further oxidation by the catalyst in the organic phase, thereby minimizing the formation of compounds having three or more hydroxyl groups. Thus, in the process of the present invention, the adamantanediol is produced in high selectivity.

Alternatively, after the hydroxylation is completed, alcohol having 4 to 8 carbon atoms may be added to the reaction liquid to transfer the adamantanediols from the water phase into the organic phase. When the addition of the alcohol is intended, the hydroxylation of the adamantane compound is particularly preferred to be carried out in two-phase system of water and ethyl acetate. For example, when 12% by weight aqueous solution of sodium hypochlorite is used, a part of the adamantanediols formed is not dissolved in the reaction liquid and suspended therein. The suspended adamantanediols come to be dissolved in the organic phase by the addition of alcohol, thereby making the adamantanediols extractable with organic solvent. The ruthenium compound remaining in the organic phase after the phase separation is reduced by the alcohol being added and precipitated. The precipitated ruthenium compound is recovered by centrifugal sedimentation. The recovered ruthenium compound is reused in the next run of reaction.

The alcohol having 4 to 8 carbon atoms may include 1-butanol, 2-butanol, 2-methyl-1-propanol, 1-pentanol, 3-pentanol, 3-methyl-1-butanol, 2-methyl-2-butanol, 1-hexanol, 4-methyl-2-pentanol, 2-ethyl-1-butanol, cyclohexanol, 1-heptanol, 1-octanol and benzyl alcohol. Of the above alcohols, preferred are 1-butanol, 1-pentanol, 1-hexanol, 2-butanol, 2-methyl-1-propanol, 3-methyl-1-butanol and benzyl alcohol.

The alcohol is used in an amount of 4 to 50 parts by weight, preferably 5 to 30 parts by weight per one part by weight of the adamantanediols formed in the reaction liquid. When the amount is less than the above range, the adamantanediols are not completely dissolved to make the extraction inefficient. An amount exceeding the above range increases the amount of organic phase to result in a large energy cost for concentration to separate the adamantanediols.

The extraction temperature is 10 to 80° C., preferably 20 to 70° C. When the temperature is low than the above range, a larger amount of alcohol is required due to a reduced solubility of the adamantanediols. When the temperature is higher than the above range, the extraction operation is impeded due to boiling of the organic solvent. The adamantanediols are separated from the organic phase by known methods such as filtration, condensation, distillation, crystallization and recrystallization.

In the present invention, prior to the addition of the alcohol to the reaction liquid, the ruthenium compound catalyst in the organic phase may be transferred into the water phase by adding alkali to the reaction liquid, thereby efficiently removing the ruthenium compound catalyst from the reaction liquid and facilitating the extraction of the adamantanediols. Specifically, the ruthenium compound is transferred into the water phase by adding alkali to the reaction liquid in an amount sufficient for making the water phase pH 7 or more.

The alkali usable may include metal hydroxides such as sodium hydroxide, potassium hydroxide, lithium hydroxide and barium hydroxide; and tetralkylammonium hydroxides such as tetramethylammonium hydroxide, tetraethylammonium hydroxide, tetrapropylammonium hydroxide and tetrabutylammonium hydroxide. Preferred are sodium hydroxide and potassium hydroxide. Alkali may be added directly or added dropwise in the form of aqueous solution.

After transferring the ruthenium compound into the water phase by adding alkali, the alcohol is added to the reaction liquid in the manner mentioned above. By these treatments, the adamantanediols and the ruthenium compound are separated into the organic phase and the water phase in the reaction system, respectively. From the organic phase, the adamantanediols are obtained. Since the ruthenium compound is reduced in the water phase and precipitated as black insolubles, the solid ruthenium compound is easily recovered by filtration and reused in the next run of reaction.

The present invention will be described in further detail by way of the following Examples. However, it should be construed that the following examples are merely illustrative and not intended to limit the invention thereto.

EXAMPLE 1

Into a 200-ml five-necked flask equipped with a stirring device, a thermometer, a Dimroth condenser and a pH electrode, were charged 5.11 g (37.5 mmol) of adamantane, 95.7 g of 1,2-dichloroethane, 0.78 g (3.2 mmol as dihydrate) of $RuCl_3$.n-hydrate and 10.5 g of water. After heating to 50° C., 100 g of aqueous solution of sodium hypochlorite (0.75 mmol/g) were added dropwise to the mixture over 160 minutes while controlling the dropping speed so as to maintain the reaction pH not exceeding pH 3. After completing the reaction, the resultant reaction liquid was separated into the water phase and the dichloroethane phase by a separation funnel. The respective phases were analyzed by gas chromatography. The results showed that the water phase contained 0.03 g of 1-adamantanol and 2.25 g of 1,3-adamandanediol, and the dichloroethane phase contained 2.47 g of 1-adamantanol, 0.52 g of 1,3-adamantanediol and 0.14 g of 2-adamantanone. The conversion of adamantane was 100%, the selectivity of 1-adamantanol was 44% and the selectivity of 1,3-adamantanediol was 44%, each based on adamantane.

EXAMPLE 2

The procedures of Example 1 were repeated except that 100 g of aqueous solution of sodium hypochlorite (0.75 mmol/g) were added dropwise over 160 minutes while controlling the dropping speed so as to maintain the reaction pH not exceeding pH 7. The results of gas chromatographic analysis showed that the water phase contained 0.03 g of 1-adamantanol and 1.36 g of 1,3-adamandanediol, and the dichloroethane phase contained 2.01 g of 1-adamantanol, 0.43 g of 1,3-adamantanediol and 0.15 g of 2-adamantanone. The conversion of adamantane was 100%, the selectivity of 1-adamantanol was 36% and the selectivity of 1,3-adamantanediol was 28%, each based on adamantane.

EXAMPLE 3

The procedures of Example 1 were repeated except that the reaction temperature was changed to 40° C. and 100 g of aqueous solution of sodium hypochlorite (0.75 mmol/g) were added dropwise over 242 minutes while controlling the dropping speed so as to maintain the reaction pH not exceeding pH 3. The results of gas chromatographic analysis showed that the water phase contained 0.04 g of 1-adamantanol and 1.38 g of 1,3-adamandanediol, and the dichloroethane phase contained 2.95 g of 1-adamantanol, 0.40 g of 1,3-adamantanediol and 0.15 g of 2-adamantanone. The conversion of adamantane was 100%, the selectivity of 1-adamantanol was 53% and the selectivity of 1,3-adamantanediol was 29%, each based on adamantane.

EXAMPLE 4

The procedures of Example 1 were repeated except that 41.9 g of aqueous solution of sodium hypochlorite (1.79 mmol/g) were added dropwise over 100 minutes while controlling the dropping speed so as to maintain the reaction pH not exceeding pH 3. During the reaction, white solid matters attributable to 1,3-adamatanediol appeared. The results of gas chromatographic analysis showed that the water phase contained 0.02 g of 1-adamantanol and 0.83 g of 1,3-adamandanediol, and the dichloroethane phase contained 3.58 g of 1-adamantanol, 0.67 g of 1,3-adamantanediol and 0.17 g of 2-adamantanone. The conversion of adamantane was 100%, the selectivity of 1-adamantanol was 64% and the selectivity of 1,3-adamantanediol was 24%, each based on adamantane.

EXAMPLE 5

The procedures of Example 1 were repeated except that 33.4 g of 1,2-dichloroethane, 0.26 g (1.1 mmol as dihydrate) of $RuCl_3$.n-hydrate and 3.2 g of water were used and 100 g of aqueous solution of sodium hypochlorite (0.75 mmol/g) were added dropwise over 176 minutes while controlling the dropping speed so as to maintain the reaction pH not exceeding pH 7. The results of gas chromatographic analysis showed that the water phase contained 0.07 g of 1-adamantanol and 2.30 g of 1,3-adamandanediol, and the dichloroethane phase contained 2.52 g of 1-adamantanol, 0.67 g of 1,3-adamantanediol and 0.35 g of 2-adamantanone. The conversion of adamantane was 100%, the selectivity of 1-adamantanol was 45% and the selectivity of 1,3-adamantanediol was 43%, each based on adamantane.

EXAMPLE 6

Into a 2-liter separable flask equipped with a stirring device, a thermometer, a Dimroth condenser and a pH electrode, were charged 68.6 g (503 mmol) of adamantane, 800 ml of ethyl acetate, 10.5 g (43.1 mmol as dihydrate) of $RuCl_3$.n-hydrate and 70.9 g of water. After heating to 50° C., 1088.1 g of aqueous solution of sodium hypochlorite (0.96 mmol/g) were added dropwise to the mixture over 90 minutes while controlling the dropping speed so as to maintain the reaction pH not exceeding pH 3. After completing the reaction, the resultant reaction liquid was separated into the water phase and the ethyl acetate phase by a separation funnel. The respective phases are analyzed by gas chromatography. The results showed that the water phase contained 0.5 g of 1-adamantanol and 22.8 g of 1,3-adamandanediol, and the ethyl acetate phase contained 2.1 g of adamantane, 25.6 g of 1-adamantanol, 22.3 g of 1,3-adamantanediol and 3.1 g of 2-adamantanone. The conversion of adamantane was 97%, the selectivity of 1-adamantanol was 35% and the selectivity of 1,3-adamantanediol was 55%, each based on adamantane.

EXAMPLE 7

The procedures of Example 1 were repeated except that 29.8 g of 1,4-dichlorobutane, 0.14 g (0.58 mmol as dihydrate) of $RuCl_3$.n-hydrate and 3.0 g of water were used and 203.3 g of aqueous solution of sodium hypochlorite (0.37 mmol/g) were added dropwise at 70° C. over 125 minutes while controlling the dropping speed so as to maintain the reaction pH not exceeding pH 7. The results of gas chromatographic analysis showed that the water phase contained 0.23 g of 1-adamantanol and 2.74 g of 1,3-adamandanediol, and the dichlorobutane phase contained 2.22 g of 1-adamantanol, 0.12 g of 1,3-adamantanediol and 0.26 g of 2-adamantanone. The conversion of adamantane was 99.4%, the selectivity of 1-adamantanol was 43% and the selectivity of 1,3-adamantanediol was 46%, each based on adamantane.

EXAMPLE 8

Into a 10-liter jacketed glass reactor equipped with a stirring device, a thermometer, a Dimroth condenser and a pH electrode, were charged 408.8 g (3 mol) of adamantane, 3200 ml of ethyl acetate, 20 g (82.1 mmol as dihydrate) of $RuCl_3$.n-hydrate and 720 g of water. To the resultant mixture, 4285 g of 12% by weight aqueous solution of sodium hypochlorite were added dropwise at 50° C. After the reaction was completed, 100 g of 20% by weight aqueous solution of sodium hydroxide were added dropwise over 20 minutes under mild stirring to make the water phase to pH 9.0. After completion of adding the aqueous solution of sodium hydroxide, the water phase became black suspension and the organic phase was clear with no color. After adding 4000 ml of 1-hexanol, the stirring was further continued for 30 minutes at 40° C., followed by phase separation. After re-extracting the water phase with 1000 ml of 1-hexanol, the combined organic phase was concentrated and filtered to obtain 264 g of 1,3-adamantanol crystals. Separately, 27 g of ruthenium compound were recovered by filtering the water phase.

EXAMPLE 9

The procedures of Example 8 were repeated except for using 1-pentanol in place of 1-hexanol to obtain 257 g of 1,3-adamantanediol crystals.

EXAMPLE 10

The procedures of Example 8 up to the addition of sodium hydroxide were repeated. Then, after adding 3200 ml of 1-butanol, the stirring was continued for 30 minutes at 40° C., followed by phase separation. The organic phase was concentrated and filtered to obtain 251 g of 1,3-admandanediol crystals.

EXAMPLE 11

The procedures of Example 10 were repeated except for using benzyl alcohol in place of 1-butanol to obtain 250 g of 1,3-adamantanediol crystals.

As described above, the process of the present invention produces the adamantanols in high selectivity and high yields. The adamantanediols may be transferred into the organic phase and the catalyst may be transferred into the water phase. This enables the efficient separation and recovery of the adamantanediols and the catalyst by simplified operations and apparatus. Further, since the reaction products are separated in the reaction vessel, the number of components for the apparatus is reduced.

What is claimed is:

1. A process of producing adamantanols comprising a step of hydroxylating an adamantane compound in the presence of a ruthenium compound and hypochlorous acid or its salts, wherein said hydroylation is carried out in two-phase system of water and organic solvent, and wherein an alcohol having 4 to 8 carbon atoms is added to a reaction liquid after the hydroxylation of the adamantane compound, thereby transferring adamantanediols into the organic phase.

2. The process according to claim 1, wherein said adamantane compound is represented by the following formula:

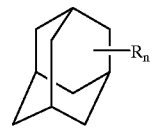

wherein $R_n$ is independently alkyl group, aryl group, cycloalkyl group, alkoxyl group, aryloxy group, acyloxy group or halogen atom, and suffix "n" is an integer from 0 to 14, with the proviso that at least two bridge-head carbons are not substituted by $R_n$.

3. The process according to claim 1, wherein said organic solvent is selected from the group consisting of alkyl halides, aryl halides, esters and hydrocarbons.

4. The process according to claim 1, said organic solvent is 1,2-dichloroethane or ethyl acetate.

5. The process according to claim 1, wherein said ruthenium compound is selected from the group consisting of metallic ruthenium, ruthenium dioxide, ruthenium hydroxide, ruthenium chloride, ruthenium bromide, ruthenium iodide, ruthenium sulfate, ruthenium tetraoxide and hydrates thereof.

6. The process according to claim 1, wherein said adamantane compound is hydroxylated at 10 to 100° C. for 200 to 500 minutes in the presence of 0.001 to 2 mol of the ruthenium compound and 0.5 to 4 mol of hypochlorous acid or its salt, each based on one mol of said adamantane compound.

7. The process according to claim 1, wherein said organic solvent is ethyl acetate.

8. The process according to claim 1, wherein said alcohol having 4 to 8 carbon atoms is selected from the group consisting of 1-butanol, 2-butanol, 2-methyl-1-propanol, 1-pentanol, 3-pentanol, 3-methyl-1-butanol, 2-methyl-2-butanol, 1-hexanol, 4-methyl-2-pentanol, 2-ethyl-1-butanol, cyclohexanol, 1-heptanol, 1-octanol and benzyl alcohol.

9. The process according to claim 1, said alcohol having 4 to 8 carbon atoms is selected from the group consisting of 1-butanol, 1-pentanol, 1-hexanol, 2-butanol, 2-methyl-1-propanol, 3-methyl-1-butanol and benzyl alcohol.

10. The process according to claim 1, wherein an addition amount of said alcohol having 4 to 8 carbon atoms is 4 to 50 parts by weight based on one part by weight of the adamantanediols in the reaction liquid.

11. The process according to claim 1, wherein an alkali is added to the reaction liquid prior to the addition of said alcohol having 4 to 8 carbon atoms, thereby transferring the ruthenium compound into the water phase.

12. The process according to claim 11, wherein said alkali is added in an amount sufficient for making the water phase to pH 7 or higher.

13. The process according to claim 1, wherein said ruthenium compound is selected from the group consisting of metallic ruthenium, ruthenium dioxide, ruthenium hydroxide, ruthenium chloride, ruthenium bromide, ruthenium iodide, ruthenium sulfate, ruthenium tetraoxide and hydrates thereof.

14. The process according to claim 1, wherein said adamantane compound is hydroxylated at 10 to 100° C. for 200 to 500 minutes in the presence of 0.001 to 2 mol of the ruthenium compound and 0.5 to 4 mol of hypochlorous acid or its salt, each based on one mol of said adamantane compound.

* * * * *